(12) United States Patent
Olivier et al.

(10) Patent No.: US 6,630,112 B2
(45) Date of Patent: Oct. 7, 2003

(54) PROCESS AND UNIT FOR CARRYING OUT A REACTION ON AN ORGANIC FEED, SUCH AS DIMERIZATION OR METATHESIS, IN THE PRESENCE OF A POLAR PHASE CONTAINING A CATALYST

(75) Inventors: Helene Olivier, Rueil Malmaison (FR); Dominique Commereuc, Meudon (FR); Alain Forestiere, Vernaison (FR); Francois Hugues, Charly Vernaison (FR)

(73) Assignee: Institut Français du Pétrole, Rueil-Malmaison (FR)

( * ) Notice: Subject to any disclaimer, the term of this patent is extended or adjusted under 35 U.S.C. 154(b) by 234 days.

(21) Appl. No.: 09/779,649

(22) Filed: Feb. 9, 2001

(65) Prior Publication Data

US 2001/0005494 A1 Jun. 28, 2001

Related U.S. Application Data

(62) Division of application No. 09/084,353, filed on May 27, 1998, now Pat. No. 6,284,937.

(30) Foreign Application Priority Data

May 27, 1997 (FR) ............................................. 97 06571

(51) Int. Cl.$^7$ .............................. C08F 2/00; B01J 8/00; B01J 8/08
(52) U.S. Cl. ....................... 422/132; 422/131; 422/134; 422/188; 422/189; 422/190; 422/195; 422/234
(58) Field of Search ................................ 422/131–138, 422/188, 189, 196, 194, 195, 198, 234, 235

(56) References Cited

U.S. PATENT DOCUMENTS

| | | | |
|---|---|---|---|
| 2,755,324 A | 7/1956 | Mueller | 260/683.15 |
| 5,104,840 A | 4/1992 | Chauvin et al. | 502/117 |
| 5,723,712 A | 3/1998 | Chauvin et al. | 585/513 |
| 5,728,353 A | * 3/1998 | Govoni et al. | 422/145 |

FOREIGN PATENT DOCUMENTS

FR 2611700 3/1987

\* cited by examiner

Primary Examiner—Jerry D. Johnson
Assistant Examiner—Alexa Ann Doroshenk
(74) Attorney, Agent, or Firm—Millen, White, Zelano & Branigan, P.C.

(57) ABSTRACT

A process for carrying out a reaction on an organic feed, for example dimerization, co-dimerization, oligomerization or metathesis of olefins, as described in which the catalyst is a catalytic metal compound dissolved in a non-aqueous ionic medium which is not or is only slightly miscible with hydrocarbons. The reaction is carried out in a system comprising at least two treatment loops each comprising at least one reaction zone and at least one zone for separating the organic and polar phases between which the polar medium containing the catalytic metal compound, and the organic phase circulate. Fresh polar phase is injected into the second loop and used polar phase is eliminated from the first loop. The hydrocarbon to be transformed is injected into the first loop and the products are withdrawn from the second loop. The invention also concerns a unit for carrying out the process.

13 Claims, 1 Drawing Sheet

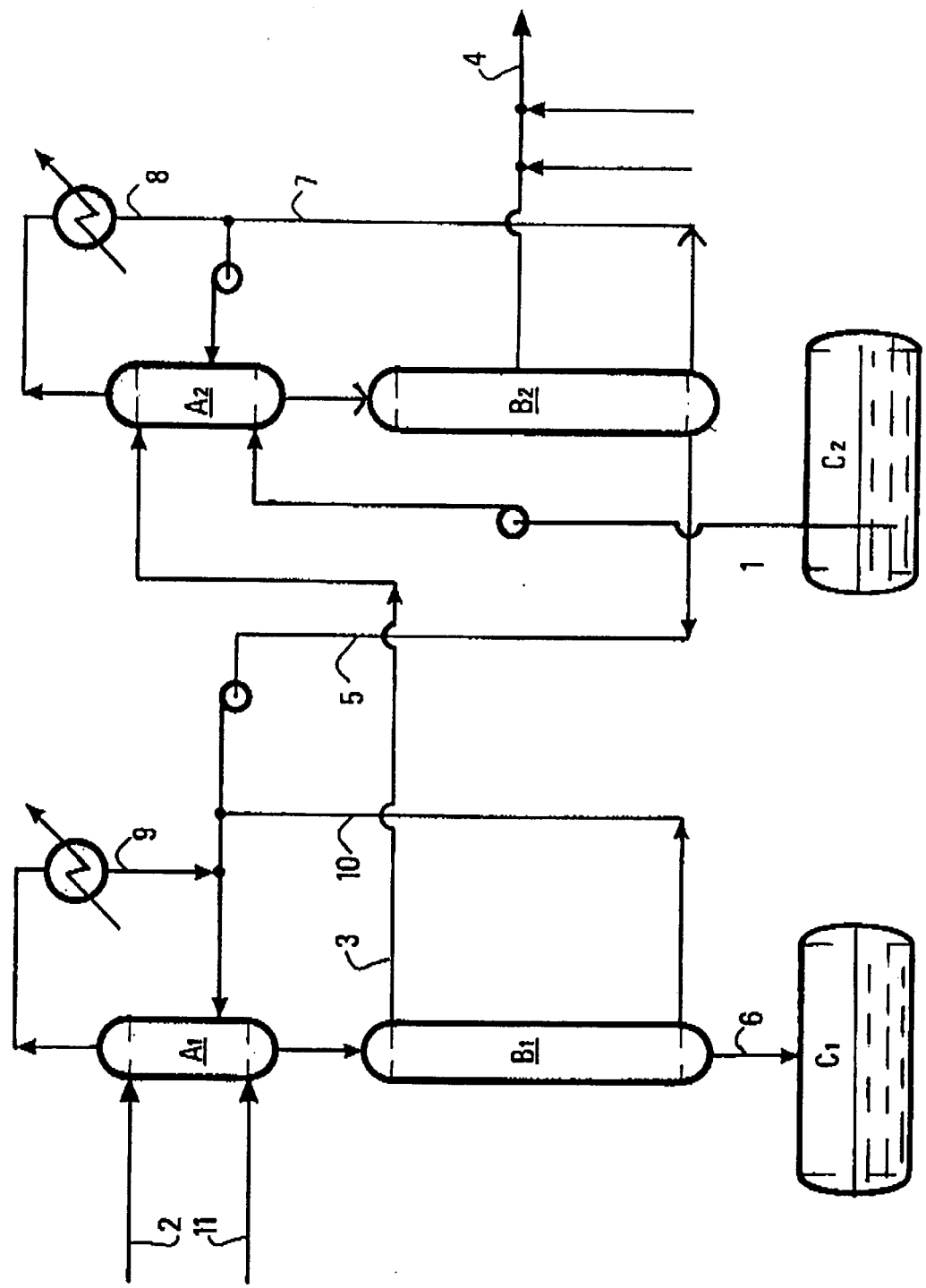

PROCESS AND UNIT FOR CARRYING OUT A REACTION ON AN ORGANIC FEED, SUCH AS DIMERIZATION OR METATHESIS, IN THE PRESENCE OF A POLAR PHASE CONTAINING A CATALYST

This is a division, of application Ser. No. 09/084,353 filed May 27, 1998 now U.S. Pat. No. 6,284,937.

SUMMARY OF THE INVENTION

The present invention relates to an improved two-phase process for carrying out a continuous reaction (such as dimerisation, co-dimerisation, oligomerisation or metathesis of olefins) on an organic feed, using a catalyst which contains at least one catalytic clement, dissolved in a non-aqueous ionic medium which is not or is only slightly miscible with the olefins. In other words, it relates to a process for carrying out a two-phase catalyzed reaction. The invention also relates to a unit for carrying out the process.

As described above, a two-phase system has the advantage of using the catalyst better than using a single-phase, homogeneous system. However, continuous economic implementation of a two-phase system poses a certain number of problems, such as interference with the catalyst and with the polar phase by trace impurities contained in the feeds. Such impurities are water, alcohols, ethers, nitrogen-containing compounds and sulphur-containing compounds. They react with the catalyst-polar phase complex.

The process of the invention consists of circulating a counter-current of feed and polar phase in at least two treatment loops. This results in a pre-treatment of the feed in the first loop by used catalytic composition, i.e., that which has lost the majority of its activity, the used catalytic composition originating from the second loop, and then being withdrawn from the process. This implementation reduces consumption of the catalyst-polar phase system, avoids the need for a section for eliminating the transition element and enables the catalyst to be treated off-site.

The process of the invention is a process for carrying out a reaction on an organic feed, in the presence of a polar phase containing at least one catalytic composition resulting from mixing: at least one non-aqueous ionic medium which is not or is only slightly miscible with the organic phase; at least one compound of a catalytic element; and optionally at least one co-catalyst.

In the process of the invention, the feed to be treated and the non-aqueous medium circulate as a counter-current between at least two treatment loops, each loop comprising at least one reaction zone connected to at least one zone for separating the organic and polar phases, the feed to be treated being supplied to the reaction zone of the first loop and fresh non-aqueous ionic medium, i.e., as yet unused, being introduced to the reaction zone in the second or final loop. The other constituent(s) of the catalytic composition can be introduced to any part of the process. The polar phase separated in the separation zone of the second loop or from each of the subsequent loops is sent to the reaction zone of the first loop or respectively the preceding loop, while the organic phase separated in the separation zone of the first loop or its subsequent loops is sent to the reaction zone of the second loop or respectively its subsequent loop. The organic phase obtained from the separation zone of the final loop and the polar phase obtained from the separation zone of the first loop are withdrawn from the process.

In a preferred variation, a portion of the reaction medium from one reaction zone is withdrawn from one part of said zone for re-injection into said zone.

Advantageously, at least a portion of the polar phase withdrawn from one separation zone of a loop is recycled to the reaction zone of the same loop.

Preferably, said fresh non-aqueous ionic medium also comprises at least a portion of at least one constituent of the catalytic composition. In that case, advantageously, the fresh non-aqueous ionic medium introduced to part of the final loop also comprises at least one transition element compound.

Preferably again, at least a portion of at least one constituent of the catalytic composition is introduced to part of the reaction zone of the first loop. Again advantageously, fresh co-catalyst is introduced into the reaction zone of the first loop.

In one implementation of the invention, a fresh catalytic composition comprising fresh non-aqueous ionic medium and at least one transition element compound and optionally at least one co-catalyst are introduced into the reaction zone of the last loop.

In the two-loop implementation illustrated below, the process comprises a first and a second treatment loop, each comprising a reaction zone (respectively $A_1$ and $A_2$) connected to a separation zone (respectively $B_1$ and $B_2$), the feed to be treated is supplied to the first reaction zone $A_1$, also co-catalyst, fresh non-aqueous ionic medium mixed with at least one transition element compound and optionally at least a portion of the co-catalyst being supplied to the second reaction zone $A_2$;

the polar phase separated from separation zone $B_2$ is introduced into the reaction zone $A_1$, while the organic phase separated in separation zone $B_1$ is introduced into reaction zone $A_2$;

the organic phase containing the reaction products separated in separation zone $B_2$ and the used polar phase separated in separation zone $B_1$ being withdrawn from the process.

In one implementation, for example, a portion of the reaction medium is withdrawn from the reaction zone of the second loop, cooled and re-injected into that zone.

The non-aqueous ionic medium comprises at least one salt known as a "molten salt" and preferred salts of the invention have general formula $Q^+A^-$ where $A^-$ represents a non co-ordinating or slightly co-ordinating anion. Preferred compounds are those which can form a liquid salt at low temperature, i.e., below 150° C. and advantageously at most 80° C., preferably below 50° C., for example halogenoaluminates, organohalogenoaluminates, halogenogallates, and organohalogenogallates. $Q^+$ represents a quaternary ammonium and/or quaternary phosphonium ion. The quaternary ammonium and/or phosphonium ions preferably have general formulae $NR^1R^2R^3R^{4+}$ and $PR^1R^2R^3R^{4+}$ or general formulae $R^1R^2N=CR^3R^{4+}$ and $R^1R^2P=CR^3R^{4+}$ where $R^1$, $R^2$, $R^3$ and $R^4$, which may be identical or different, represent hydrogen with the exception of the cation $NH_4^+$, and preferably a single substituent represents hydrogen, or hydrocarbyl residues containing 1 to 12 carbon atoms, for example saturated or unsaturated alkyl groups, cycloalkyls or aromatics, aryl or aralkyl groups, containing 1 to 12 carbon atoms. The ammonium and/or phosphonium ions can also be derivatives of nitrogen-containing or phosphorus-containing heterocycles containing 1, 2 or 3 nitrogen and/or phosphorous atoms, with general formulae:

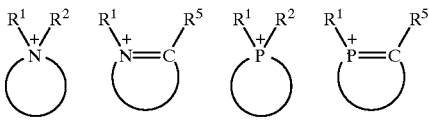

where the cycles are constituted by 4 to 10 atoms, preferably 5 or 6 atoms, $R^1$ and $R^2$ being defined as above. The quaternary ammonium or phosphonium ion can also be, a cation with formula:

$$R^1R^{2+}N=CR^3-R^5-R^3C=N^+R^1R^2$$

$$R^1R^{2+}P=CR^3-R^5-R^3C=P^+R^1R^2$$

where $R^1$, $R^2$ and $R^3$, which may be identical or different, are defined as above and $R^5$ represents an alkylene or phenylene residue. The following $R^1$, $R^2$, $R^3$ and $R^4$ groups can be mentioned: methyl, ethyl, propyl, isopropyl, butyl, secondary butyl, tertiary butyl, amyl, methylene, ethylidene, phenyl or benzyl radicals; $R^5$ may be a methylene, ethylene, propylene or phenylene group. The ammonium and/or phosphonium cation is preferably selected from the group formed by N-butylpyridiunium, N-ethylpyridinium, 3-butyl-1-methylimidazolium, diethylpyrazolium, 3-ethyl-1-methylimidazolium, pyridinium, trimethylphenylammonium, 3-ethyl-1-methylimidazolium, and tetrabutylphosphonium.

These salts can be used alone or as a mixture. They act as a solvent.

For dimerisation, co-dimerisation, or oligomerisation, for example, the polar phase of the invention can also comprise a mixture of at least one lithium halide with at least one hydrocarbylaluminium halide (as described in European patent application EP-A-0 753 346).

In a further implementation, it can comprise a mixture of at least one ammonium halide or quaternary pheosphonium halide with at least one aluminium halide and/or at least one hydrocarbylaluminium dihalide (as described in EP-A-0 448 445, French patent FR-A2 2 611 700 and EP-A-0 646 412). Nickel is the preferred catalytic element.

The preferred polar phase of the invention comprises (or advantageously is constituted by) a mixture of at least one aluminium halide or respectively at least one hydrocarbylaluminium halide with at least one quaternary ammonium halide and/or quaternary phosphonium halide, or respectively a lithium halide, and advantageously in a molar ratio of aluminium compound/molten salt which is in the range 1 to 2, preferably 1.1 to 1.6.

The hydrocarbylaluminium halide has general formula $Al_2X_xR_{6-x}$ where X is chlorine or bromine, R is an alkyl, cycloalkyl, aryl or aralkyl radical comprising 1 to 10, preferably 2 to 6, carbon atoms, x taking the values 2, 3 or 4. They can be used alone or as a mixture. Examples are alkylaluminium chlorides such as ethylaluminium dichloride, isobutylaluminium dichloride, ethylaluminium sesquichloride and diethylaluminium chloride.

The catalytic element (generally a transition metal from groups 6, 8, 9 or 10) is used in the form of a salt such as a carboxylate, acetylacetonate, chloride, bromide, sulphate, nitrate or complexes which these salts form with phosphines, amines, or nitriles. Other compounds may also be suitable.

The concentration of transition metal compound in the polar phase is advantageously in the range 1 mmole per liter to 500 mmoles per liter, preferably in the range 2 to 300 mmoles per liter.

The invention is not limited to the catalytic compositions described above; other compositions may be suitable for dimerisation, co-dimerisation or oligomerisation.

For metathesis, for example, it is possible to use a composition as described in French patent application FR-A-2 715 328, comprising at least one ammonium halide and/or quaternary phosphonium halide mixed with at least one aluminium halide and at least one organometallic aluminium compound. This latter generally has formula $Al_2X_xR_{3-x}$ where R is a linear or branched alkyl radical containing 2 to 8 carbon atoms, X is chlorine or bromine and x equals 1, 2 or 3. The catalytic element is tungsten or molybdenum (group 6).

Other catalysts may be suitable.

More generally, the catalyst selected is that which is suitable for the desired reaction.

The reaction mixture comprises a hydrocarbon phase constituted by reactants, products and inert constituents, and the polar phase contains the dissolved transition metal complex.

The temperatures at which the reaction and separation are carried out are generally substantially identical and are generally in the range −20° C. to +80° C., preferably −10° C. to +60° C., The pressure is sufficient to maintain all of the reactants and constituents of the cuts in the liquid phase, i.e., in the complete absence of a gas phase. The operating conditions are clearly those necessary for carrying out the desired reaction.

The invention also relates to a unit for carrying out the reaction in a non-aqueous ionic medium which is not or is only slightly miscible with olefins, comprising:

at least two reaction zones $A_1$ and $A_2$;

at least two separation zones $B_1$ and $B_2$ for separating the hydrocarbon phase from the polar phase, said zones being connected to the reaction, ones $A_1$ and $A_2$;

at least one conduit 1 for introducing polar phase into reaction zone $A_2$;

at least one conduit 2 for introducing olefin food into reaction zone $A_1$;

at least one conduit 3 for supplying hydrocarbon phase separated in separation zone $B_1$ to reaction zone $A_2$;

at least one conduit 4 for withdrawing hydrocarbon phase separated in separation zone $B_2$;

at least one conduit 5 for sending die polar phase separated in separation zone $B_2$ to reaction zone $A_1$;

at least one conduit 6 for withdrawing used polar phase separated in separation zone $B_1$.

The unit preferably also comprises the following means, taken alone or in combination:

at least one conduit 7 connecting separation zone $B_2$ to reaction zone $A_2$ to recycle the polar phase;

at least one conduit 8 for withdrawing a portion of the reaction medium from zone $A_2$ and re-introducing it to said zone;

at least one conduit 9 for withdrawing a portion of the reaction medium from zone $A_1$ and re-introducing it to said zone;

at least one conduit 10 connecting separation zone $B_1$ to zone $A_1$ for recycling the polar phase;

at least one conduit 11 for introducing the reactants into the unit.

Conduits 8 and 9 advantageously comprise heat exchangers.

BRIEF DESCRIPTION OF THE DRAWING

The process and unit will be better understood from the description of

The FIGURE. FIG. 1 shows a two-loop embodiment of a unit for carrying out the process.

In the FIGURE, the reaction system comprises two treatment loops I and II constituted by reaction zones $A_1$ and $A_2$ and separation zones $B_1$ and $B_2$. Reaction zones $A_1$ and $A_2$ are constituted, for example, by a reactor provided with a mechanical stirring system and cooled externally and/or internally, or a reactor provided with external recirculation with a heat exchanger, or a tube reactor acting as a heat exchanger. Separation zones $B_1$ and $B_2$ are constituted, for example, by a vertical receptacle the height of which is sufficient to ensure proper decanting of the polar phase. A regulation system ensures that the level of polar phase in the separator is constant The olefin feed enters loop I and used polar catalytic phase leaves this same loop. Fresh polar catalytic phase enters loop II and the organic phase leaves this same loop.

Thus the olefin(s), pure or mixed with saturated hydrocarbons such as those obtained from refining processes, are continuously introduced into reaction zone $A_1$ via conduit 2. All or part of a constituent of the catalyst is also introduced into zone $A_1$ via conduit 11, for example an organohalogenated aluminium compound, pure or diluted by a hydrocarbon (in the case of a dimerisation reaction, for example).

The "used" polar phase contained in separator $B_1$ is sent to reservoir $C_1$ via conduit 6 at a rate such that the level in separator $B_1$ remains stable. The hydrocarbon phase contained in separator $B_1$ passes into reaction zone $A_2$ via conduit 3 at the mass flow rate of the feed (full loops, no gas phase).

"Fresh" polar phase containing the catalytic clement, the nickel salt (for a dimerisation reaction, for example) and contained in reservoir $C_2$ is introduced into reaction zone $A_2$ via conduit 1.

The polar phase contained in separator $B_2$ is taken up by a pump and sent to reaction zone $A_1$ via conduit 5 at a flow rate such that the level of the polar phase in separator $B_2$ remains constant. A portion is returned to reactor $A_2$.

The hydrocarbon phase contained in separator $B_2$ is withdrawn via conduit 4 at the mass flow rate of the feed (full loops, no gas phase). It contains small quantities of organohalogenated aluminium compound and is treated with anhydrous ammonia then washed with an aqueous caustic soda solution followed by water. It then undergoes fractionation to separate unit hydrocarbons, dimers and co-dimers and higher oligomers. Reactors $A_1$ and $A_2$ are provided with external recirculation conduits, respectively 9 and 8, to ensure mixing of the two phases and to eliminate the heat of reaction through exchangers.

EXAMPLES

In the following example, which describes dimerisation of n-butenes contained in a $C_4$ cut from steam cracking of a naphtha using a nickel compound and aluminium dichloroethyl dissolved in a polar phase constituted by 1-butyl-3-methylimidazoliium chloride and aluminium chloride, illustrates the invention without limiting its scope.

EXAMPLE

The two loops were each constituted by a reactor and an exchanger, the total volume being 500 liters, also a separator. The separator was a cylindrical reservoir 5 meters high and 0.5 meters in diameter.

A $C_4$ cut constituted by 70% of n-butenes and 2% of isobutene, the remainder being constituted by alkanes, was introduced into the first loop at a flow rate of 3900 kg/hour. A solution of dichloroethylaluminium, 50% by weight in hexane, was also introduced, at a flow rate of 9.6 kg/hour.

A polar phase contained in reservoir $C_2$ and constituted by 0.577 kg of aluminium chloride, 0.622 kg of butylmethylimidazolium chloride and 50 g of anhydrous nickel chloride (aluminium chloride: imidazolium chloride molar ratio=1.22) was introduced into the second loop at a flow rate of 1.25 kg/hour. The temperature of the reaction and separation zones was kept at about 10° C.

The polar phase was taken from separator $B_2$ and sent to reaction zone $A_1$. The polar phase which accumulated in separator $B_1$ was sent to reservoir $C_1$.

On leaving separator $B_2$, the effluent passing through conduit 4 was treated with anhydrous ammonia, then with a 20% aqueous caustic soda solution and finally with water. The n-butene conversion was 80%; the products were constituted by 95% of dimers and 5% of trimers.

The example shows that the invention is particularly suitable for continuous transformation of olefins, whether it be by dimerisation, co-dimerisation, or oligomerisation, as shown, or by metatlesis, for example. The catalysts are, of course, suitable for carrying out the reaction.

The preceding examples can be repeated with similar success by substituting the generically or specifically described reactants and/or operating conditions of this invention for those used in the preceding examples.

The entire disclosure of all applications, patents and publications, cited above, and of corresponding French application No. 97/06.571, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An apparatus for conducting a process comprising catalytically reacting at least one organic compound in a liquid organic phase in the presence of a polar liquid phase containing a non-aqueous ionic medium, which is sufficiently immiscible with the organic phase that the polar and organic phases can be separated by decanting, and a catalyst, wherein the apparatus comprises:

at least first and second treatment loops connected in series for circulating the liquid organic phase and the polar liquid phase in counter-current liquid contact, each of the first and second treatment loops comprising:

at least one reaction zone for containing a reaction medium of the liquid organic and polar liquid phases in contact and connected to each reaction zone, at least one separation zone for separating the organic and polar liquid phases by decanting, at least one conduit for introducing the organic compound into the reaction zone of the first treatment loop, at least one conduit for introducing the polar liquid phase into the reaction zone of the second treatment loop, at least one conduit for supplying the polar liquid phase separated in the separation zone of the second treatment loop to the reaction zone of the first treatment loop, at least one conduit for supplying the organic phase separated in the separation zone of the first treatment loop to the reaction zone of the second treatment loop, at least one conduit for withdrawing the organic phase separated in the separation zone of the second treatment loop, and at least one conduit for withdrawing the polar liquid phase separated in the separation zone of the first treatment loop.

2. The apparatus of claim 1, wherein the apparatus comprises:
more than two treatment loops.

3. The apparatus according to claim 2, wherein the polar liquid phase comprises at least a portion of the catalyst.

4. The apparatus according to claim 3, wherein the catalyst comprises at least one transition element compound.

5. The apparatus of claim 1, further comprising a conduit for withdrawing a portion of the reaction medium from one part of the reaction zone of the second treatment loop and re-introducing it into said same reaction zone.

6. The apparatus according to claim 5, wherein the conduit for withdrawing a portion of the reaction medium from one part of a reaction zone and re-introducing it, has a heat exchanger in operative association with it.

7. The apparatus of claim 1, further comprising a conduit for withdrawing a portion of the reaction medium from one part of the reaction zone of the first treatment loop and re-introducing it into said same reaction zone.

8. The apparatus according to claim 7, wherein the conduit for withdrawing a portion of the reaction medium from one part of a reaction zone and re-introducing it, has a heat exchanger in operative association with it.

9. The process according to claim 1, in which at least a portion of the polar liquid phase withdrawn from the separation zone of the second treatment loop is recycled to the reaction zone of the second treatment loop.

10. The process according to claim 1, in which at least a portion of the polar liquid phase withdrawn from the separation zone of the first treatment loop is recycled to the reaction zone of the second treatment loop.

11. The apparatus according to claim 1, further comprising a conduit for introducing at least a portion of the catalyst to the reaction zone of the first treatment loop.

12. The apparatus of claim 1, wherein the apparatus consists of two treatment loops.

13. The apparatus according to claim 12, further comprising a conduit for withdrawing a portion of the reaction medium from the reaction zone of the second treatment loop and re-introducing into that zone and means for cooling the reaction medium in said conduit before re-introducing.

* * * * *